United States Patent [19]

Goelz

[11] Patent Number: 5,527,280
[45] Date of Patent: Jun. 18, 1996

[54] MULTI-LUMEN ENTERAL FEEDING AND MEDICATING DEVICE

[75] Inventor: Richard G. Goelz, Doylestown, Pa.

[73] Assignee: The Children's Seashore House, Philadelphia, Pa.

[21] Appl. No.: 413,093

[22] Filed: Mar. 29, 1995

[51] Int. Cl.⁶ .................................................. A61M 25/00
[52] U.S. Cl. ............................ 604/96; 604/109; 604/128
[58] Field of Search ............................... 604/96, 97, 104, 604/174, 175, 178, 180; 128/DIG. 26

[56] References Cited

U.S. PATENT DOCUMENTS

| | | | |
|---|---|---|---|
| 4,666,433 | 5/1987 | Parks | 604/178 |
| 4,685,901 | 8/1987 | Parks | 604/96 |
| 4,701,162 | 10/1987 | Rosenberg | 604/103 |
| 4,701,163 | 10/1987 | Parks | 604/178 |
| 5,234,417 | 8/1993 | Parks | 604/283 |

*Primary Examiner*—Sam Rimell
*Attorney, Agent, or Firm*—Dann, Dorfman, Herrell and Skillman; Henry H. Skillman

[57] ABSTRACT

A multi-lumen enteral feeding and medicating device having a gastric tube adapted to be introduced into the interior of a patient's stomach through a stoma. The gastric tube has a balloon to engage and seal against the interior wall of the stomach around the stoma and a locking ring to engage the skin of the patient surrounding the exterior opening of the stoma. A jejunal tube is slidably engaged in the gastric tube for relative longitudinal sliding displacement so that the distal end of the jejunal tube may be threaded through the stomach into the jejunum for introduction of a fluent material through ports adjacent the distal end of the jejunal lumen. A fluid lumen is provided in the gastric tube for applying positive and negative pressure to the interior of the balloon to extend and retract the same and an inlet attachment is provided for accessing the gastric lumen for introducing fluent material into the stomach through the gastric lumen. The jejunal tube passes through the gastric lumen and out through the inlet attachment. A sealing plug is provided to seal the inlet to the gastric lumen at the point where the jejunal tube exits the gastric lumen. The sealing plug operates to anchor the jejunal tube within the gastric lumen at the desired location which positions the distal end of the jejunal tube within the jejunum.

12 Claims, 3 Drawing Sheets

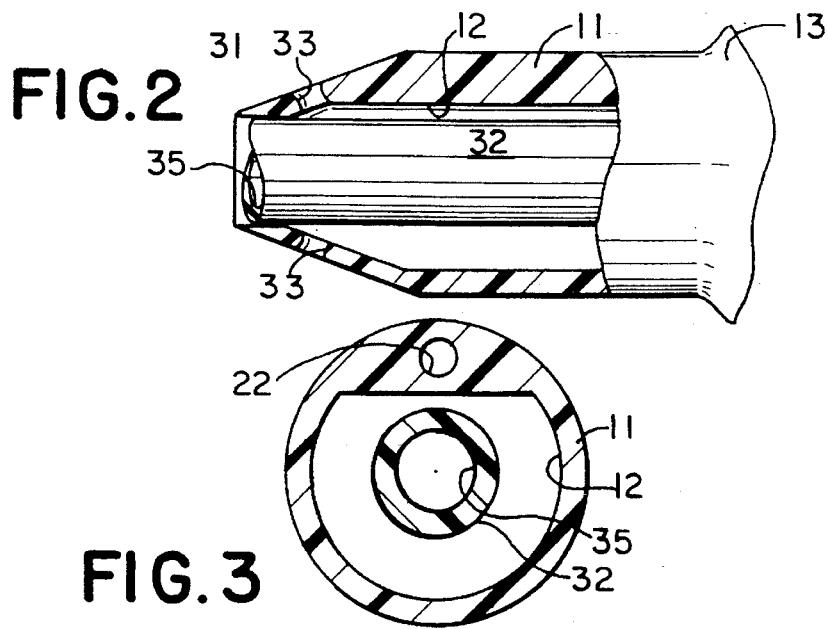
FIG. 2
FIG. 3
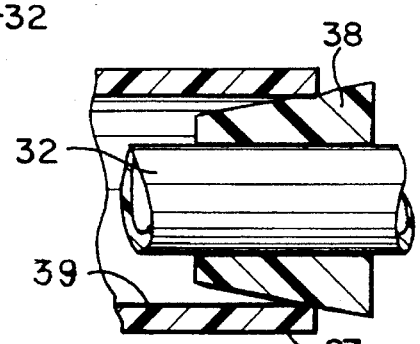
FIG. 4
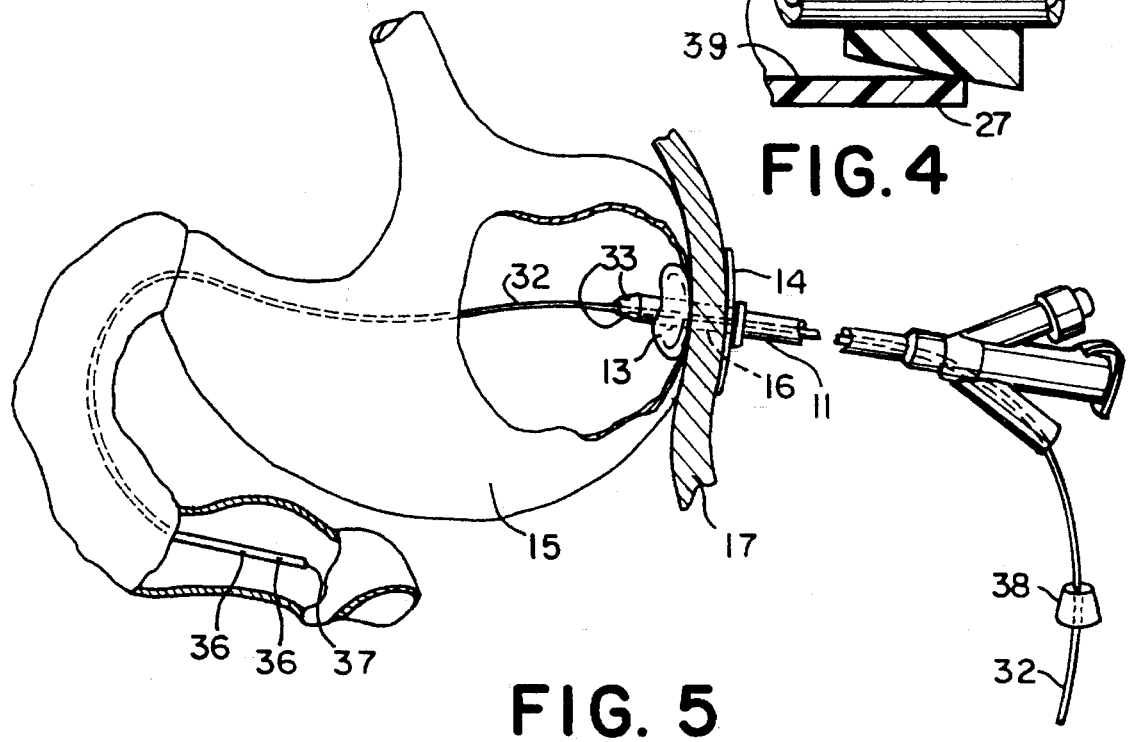
FIG. 5

MULTI-LUMEN ENTERAL FEEDING AND MEDICATING DEVICE

FIELD OF THE INVENTION

The present invention relates to a gastrointestinal or enteral feeding and medicating device which allows a single variable length appliance to accommodate pediatric as well as adult patients who require long-term gastric and jejunal feeding and medication. The invention provides a gastric feeding lumen combined with an adjustable jejunal catheter whose length can be determined at the time of clinical placement to accommodate individual patient anatomical differences. These differences are typical of the range of intestinal variations found in pediatric, post-surgical adults, and congenitally gastrointestinally abnormal patients.

The device can be employed in hospital and homecare patients to reduce the number of recurrent surgical procedures and to reduce the cost and the extent of routine nursing care required to maintain gastric stoma sites for those individuals needing long-term enteral nutrition and medication support.

BACKGROUND OF THE INVENTION

Many types of feeding catheters have been developed to provide gastric or intestinal access for patients who cannot meet their nutritional needs eating by mouth. These catheters have been designed and constructed to allow fixed length tubes for insertion through a stoma in the patient's abdomen. These devices are made to accommodate the typical adult patient anatomical sizes. They do not accommodate pediatric patients, adult patients who have undergone surgical procedures which have altered their small intestine, or those patients who suffer intestinal tract congenital abnormalities. Frequently, clinical practitioners have tried to overcome these shortcomings by inserting two tubes through the patient's abdominal stoma: one tube of the appropriate size for gastric feeding, and a second tube sized for the patient's jejunal anatomical structure.

U.S. Pat. No. 4,666,433 (S. K. Parks), U.S. Pat. No. 4,701,163 (S. K. Parks), and U.S. Pat. No. 4,701,162 (P. Rosenberg) all show such a device for gastric feeding. All of these existing tubes require a separate jejunal catheter to be placed alongside the gastric feeding device. During placement of any of the above existing tubes, the patient's stoma must be temporarily or permanently enlarged to allow both individual tubes to pass through the small abdominal opening. This is particularly aggravating in small pediatric patients. After placement, during extended use, all of these two tube methods are subject to extensive leakage of gastric contents. This is primarily due to the inability of these combinations of separate devices to seal the gastric stoma. Patients using these devices require significant routine nursing care to treat the caustic effects of stomach acid leaking onto the skin. These two tube through the stoma methods also require the patient to undergo repeated surgical procedures to excise granuloma growth at the stoma site. This granuloma growth is caused by the side to side and rotational movements of the two tubes within the stoma opening. These problems with the existing devices require the patient to undergo several costly follow-up surgical procedures and continual nursing care over extended nutritional support periods. The existing devices all require this additional medical, surgical and nursing care in the hospital setting and make home care of these patients very demanding. This combination of problems with the existing devices is particularly serious for small pediatric patients in marginal medical condition.

Gastrointestinal or enteral feeding devices currently available under U.S. Pat. Nos. 4,685,901 and 5,234,417 (S. K. Parks), have attempted to solve the previously mentioned leakage problems by employing a fixed length jejunal tube as an integral part of the device. These devices, however, do not allow clinical practitioners to adjust the length of the jejunal lumen to meet the needs of individual pediatric, post-surgical adult patients or those with congenital abnormalities. The Park devices employ only a fixed length non-adjustable tube. This makes the Park tube unusable in situations where the patient's intestinal anatomy does not match the standard length tubes currently available. This is particularly critical in pediatric and post-surgical adult patients.

SUMMARY OF THE INVENTION

None of the prior available devices solves the above problems. The present invention provides a solution with a device which has a single multiple lumen tube passing through the patient's abdominal stoma, is variable in length, and can be adjusted in the clinical setting to meet each individual patient's unique anatomical requirements.

It is an object of the present invention to provide an enteral feeding and medicating device comprising multiple lumens within a single assembly for gastric and jejunal nutrition support which has a variable length jejunal tube.

It is a further object of the present invention to provide a combined gastric and jejunal enteral feeding and medicating device that can be adjusted at the time of placement by clinical personnel to meet the individual intestinal anatomy of both pediatric and adult patients.

It is yet a further object of the present invention to provide a gastric and jejunal feeding and medicating device which reduces the need for post placement surgical procedures and nursing care for both pediatric and adult patients in the hospital and in-home care settings.

More specifically, the present invention provides an enteral device having a gastric tube adapted to pass through a stoma and to be anchored therein, along with a jejunal tube slidable interiorly of the gastric tube so as to be adjustable in its extension through the stomach and into the jejunum.

BRIEF DESCRIPTION OF THE DRAWINGS

All of the objects of the invention are more fully set forth hereinafter with reference to the accompanying drawings, wherein:

FIG. 2 is an enlarged longitudinal sectional view taken on the line 2—2 of FIG. 1;

FIG. 3 is an enlarged transverse sectional view taken on the line 3—3 of FIG. 1;

FIG. 4 is an enlarged longitudinal sectional view taken on the line 4—4 of FIG. 1

FIG. 5 is a view similar to FIG. 1 in place within a stoma, portions of the device being broken away.

DESCRIPTION OF THE PREFERRED EMBODIMENT

Figure 1:
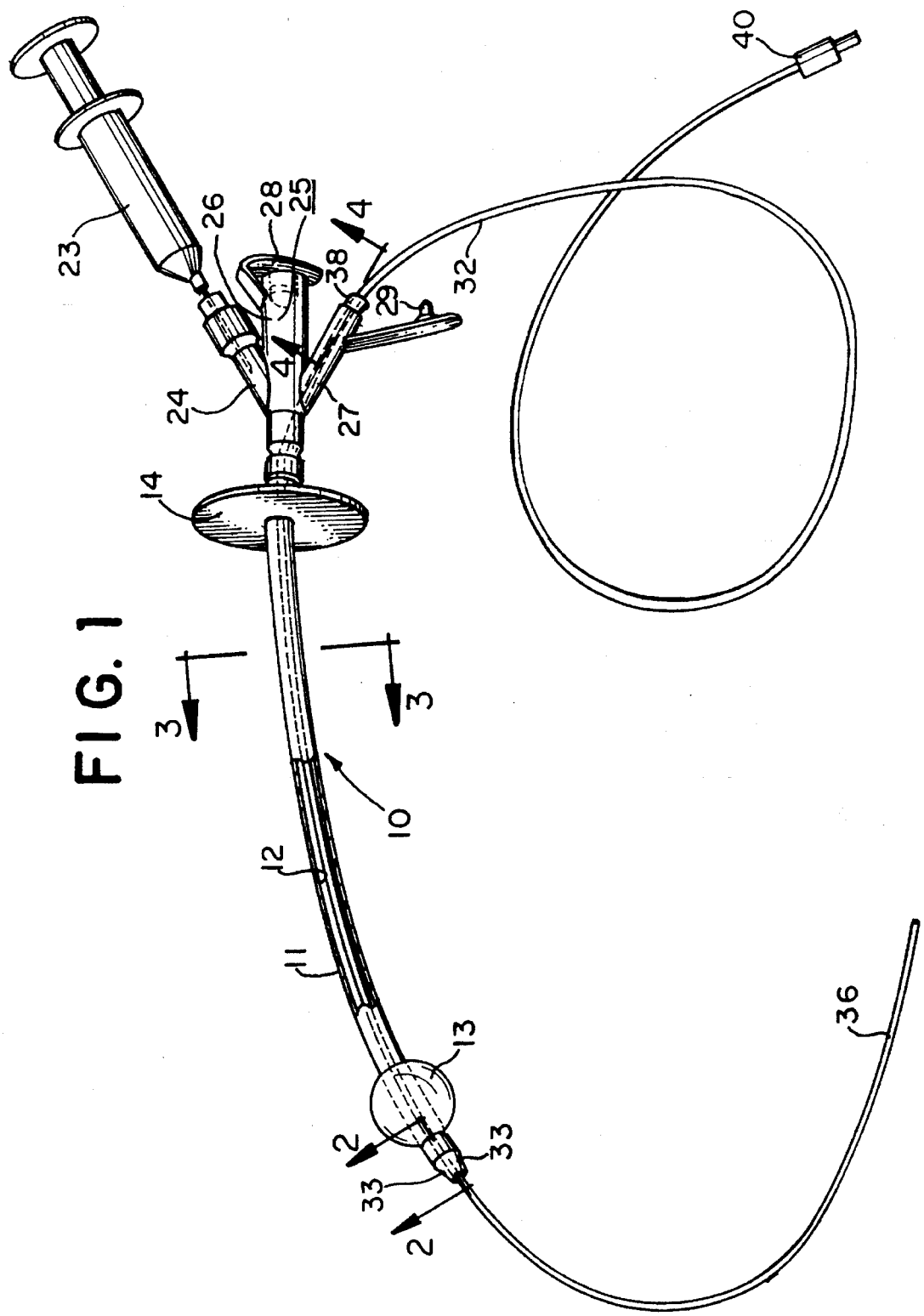
FIG. 1 is a perspective view of an enteral feeding device made in accordance with the present invention.

Referring now to the drawing, the device of the present invention is a feeding assembly 10, having a gastric feeding tube 11 with an internal bore 12 which provides a gastric lumen for introducing fluent materials into the interior of the stomach 15 through a stoma in the body wall 17 indicated by the broken lines at 16 in FIG. 5. The feeding tube 11 has a balloon 13 adjacent its distal end, which, when extended, as shown in FIG. 5, is constructed and arranged to bear against the wall of the stomach 15 surrounding the stoma 16. An anchor ring 14 cooperates with the balloon 13 to secure the gastric tube 11 in place within the stoma 16. Preferably, the mounting of the gastric tube 11 within the stoma seals the stoma against leakage or seeping of gastric juices from the stomach. As shown in FIG. 1, the sealing ring 14 is frictionally engaged with the external surface of the gastric tube 11 so that it may be displaced axially of the tube flush against the skin surrounding the stoma 14 following insertion of the gastric tube.

Figure 6:
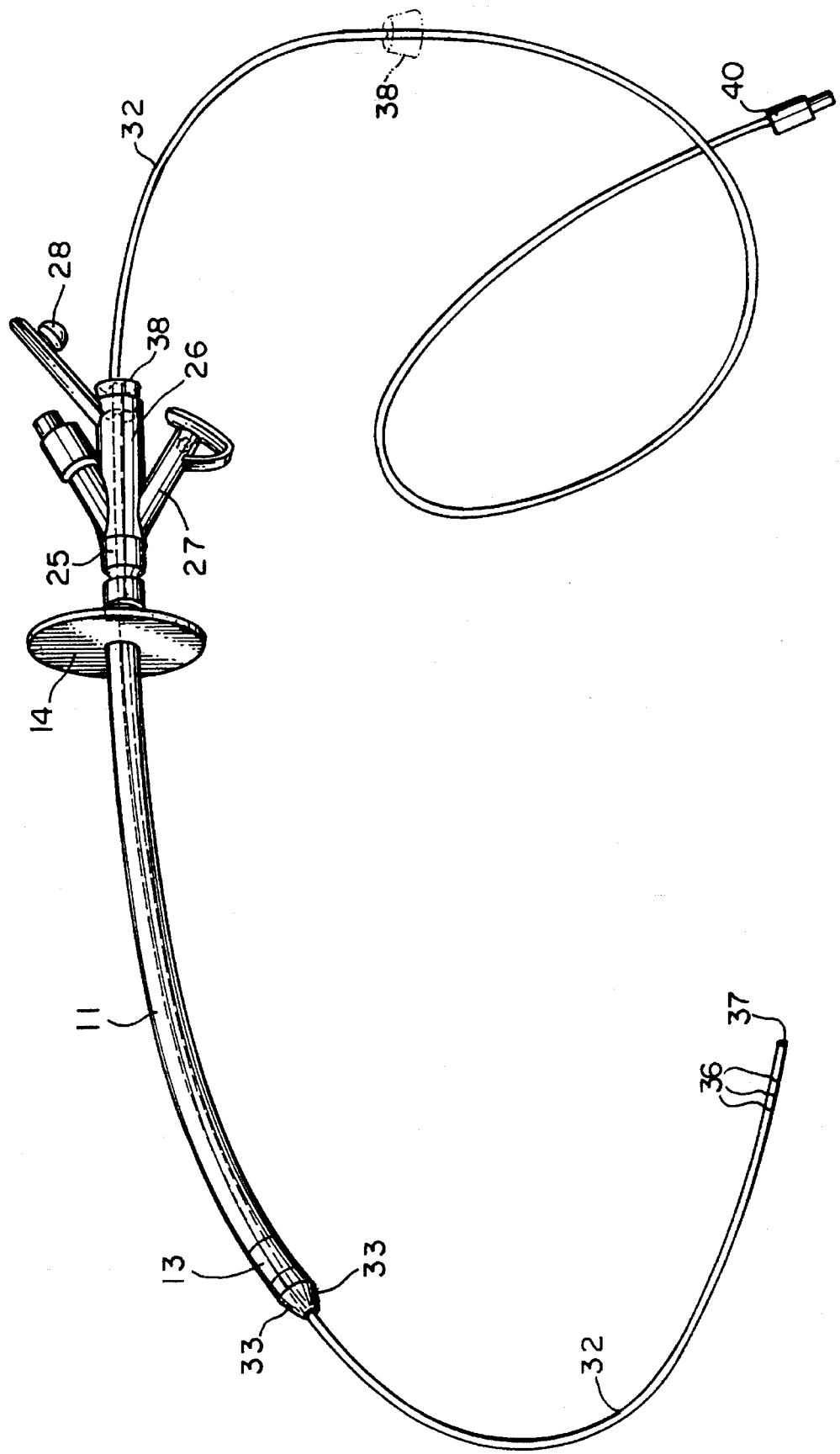
FIG. 6 is a view similar to FIG. 1 of a device made in accordance with the present invention in a different configuration.

The gastric tube includes a fluid lumen 22, in the present instance formed within the annular wall of the tube 11. Near the distal end of the tube 11, the fluid lumen 22 terminates in the interior of the balloon 13 so that upon application of positive pressure to the fluid lumen 22, the balloon 13 is extended, as shown in FIGS. 1 and 5. Upon application of negative pressure to the lumen 22, the extended balloon 13 is retracted, as shown in FIG. 6 so as to be substantially coextensive with the outline of the tube 11. After extension of the balloon as shown in FIG. 1, the gastric lumen is displaced outwardly to snugly engage the balloon against the wall of the stomach around the stoma 16, and the anchor ring 14 is slid down the exterior of the tube 11 to engage against the outer surface of the skin surrounding the stoma 16 and is held in place as shown in FIG. 5. The frictional engagement of the ring 14 on the outer surface of the tube 11 is normally sufficient to anchor the tube firmly in place and seal the stoma at the inside against leakage of gastric juices through the stoma and past the ring 14. Engaging flat against the skin around the stoma, the ring also serves to exclude leakage through the stoma to the outer skin surface.

The balloon 13 is extended and retracted by the application of positive and negative fluid pressure to the lumen 22, and this is accomplished in the conventional manner by the use of a syringe 23 which communicates with the lumen 22 through a valve 24 in a feeding attachment 25 at the inlet end of the gastric tube 11. The valve 24 comprises a conventional self-sealing plug which may be penetrated to introduce and withdraw pressure fluid from the fluid lumen 22. The valve 24 and fluid lumen 22 are isolated from the gastric lumen 12 of the gastric tube so as to not to contaminate the pressure fluid with the fluent materials introduced through the gastric lumen 12 and, vice versa, not to contaminate the fluent material in the gastric lumen with the pressure fluid from the fluid lumen 22.

The inlet attachment in addition to the branch housing the valve 24 has a main branch 26 which is axially aligned with the lumen 12 of the tube 11 and an auxiliary branch 27 which diverges from the axis of the lumen 12 at an obtuse angle. The auxiliary branch 27 has a hollow bore in communication with the hollow interior of the main branch 26 interiorly of the attachment 25. Each of the branches 26 and 27 has a cover member attached to it by a flexible tether. The main branch 26 has a cover 28 having a central plug which engages within the bore of the branch 26 to close the same. The auxiliary branch 27 has a cover 29 having a plug adapted to engage in the bore of the auxiliary branch 27.

As shown in FIG. 1, a jejunal tube 32 is adapted to be threaded through one of the branches 26 and 27, for example as shown in FIG. 1, through the branch 27. The jejunal tube 32 passes through the bore of the auxiliary branch 27 and the bore of the main branch into the bore 12 of the gastric tube 11. The jejunal tube 32 extends along the length of the gastric tube 11 and exits through its distal end. As shown in FIGS. 1 and 2, the distal end 31 of the tube 11 tapers down to snugly engage the outer perimeter of the tube 32. The tapered portion at the terminal end 31 of the tube 11 is provided with ports 33 which afford fluid communication between the interior of the stomach outside of the tube end 31 with the gastric lumen 12 on the interior of the tube end.

The jejunal tube slidably engages the tapered portion 31 and extends beyond the tapered portion into the interior of the stomach as shown in FIG. 5. The tube passes through the stomach, through the pylorus, the duodenum and into the jejunum which forms the initial sector of the small intestine. The distal end of the jejunal tube terminates in the jejunum and is provided with means to afford communication between the interior bore 35 of the jejunal tube 32 and the interior of the small intestine at the jejunum. To this end, the distal end of the tube 32 has a series of ports 36 adjacent to the terminus 37. In the present instance, the terminus 37 is closed to provide a blunt leading end thereon. The blunt leading end 37 facilitates the threading of the jejunal tube through the stomach and into the jejunum.

As shown in FIGS. 1, 4 and 5, at the inlet end of the gastric tube 11, the jejunal tube 32 passes outwardly into the gastric inlet passage within the branch 26 and branches through the jejunal passage 39 in the hollow interior of the auxiliary branch 27. After the gastric tube 11 and the jejunal tube 32 are properly positioned, the space between the jejunal tube 32 and the jejunal passage 39 is sealed with a plug 38 which is wedged between the internal wall of the passage 39 and the external surface of the jejunal tube 32. The plug 38 may be of any suitable sealing material and may incorporate an adhesive to provide a firm interlock between the jejunal tube and the fitting so as to anchor the tube against inadvertent displacement.

When assembled in this manner, as shown in FIG. 1, the jejunal tube provides access from its inlet 40 through the bore 12 of the gastric tube 11, out the terminal end 31 of the gastric tube, through the stomach and into the jejunum so as to allow the passage suitable fluent material, whether food or medication, into the jejunum, bypassing the gastric cavity of the stomach. A different fluent material may be introduced directly into the stomach through the bore 12 of the gastric tube 11 by introducing the same through the main branch 26 and through gastric lumen defined by the annular space between the jejunum tube 32 and the bore 12 of the gastric tube and out into the stomach through the ports 33.

In some instances it may be desirable to avoid even obtuse angular bends in the jejunum tube, in which event the jejunum tube may be passed through the main branch 26 instead of the auxiliary branch 27. This arrangement is shown in FIG. 6. The gastric tube 11 and the inlet attachment 25 are the same as illustrated in FIG. 1. The jejunum tube 32 is likewise is of similar design and construction, and the only difference between the arrangements shown in FIGS. 1 and 6 is that the jejunum tube is fed through the main branch 26 of the attachment 25 and the plug 38 is modified to fit between the outside of the jejunum tube 32 and the interior bore of the main branch 26. Relocating the jejunum tube into the main branch 26 frees the auxiliary branch 27 for use as an inlet passage for feeding through the gastric lumen 12 of the gastric tube 11.

The feeding and medicating device of the present invention facilitates the treatment of patients which require the introduction of different fluent materials into the stomach and the jejunum respectively. In treating such patients, the patient is provided with a stoma which affords access through the skin and stomach wall into the interior of the stomach. The stoma, as shown at 16 in FIG. 5, is created surgically and is dimensioned to snugly receive the gastric tube 11. In order to introduce the feeding and medicating device of the present invention, the jejunal tube 32 is threaded through the gastric tube 11 and is positioned with the distal end 37 extended as far as possible from the tapered end portion 31 of the gastric tube 11. A feeding wire is threaded through the bore of the jejunal tube 32 to abut the leading end 37 of the tube. The feeding wire is preferably a stiff flexible component which is opaque to electromagnetic waves so as to enable the caregiver to guide the blunt leading end 37 of the jejunal tube through the stomach, the pylorus and the duodenum into the jejunum, by observing an electromagnetic image of the stomach area. The opaque nature of the guide element serves to enable a proper positioning of the jejunal tube 32 so that its ports 36 are located within the jejunum as desired. Since the external diameter of jejunal tube is substantially smaller than the external diameter of the gastric tube 11, there is sufficient "play" between the jejunal tube 32 and the stoma to permit facile threading of the jejunal tube into the proper position within the jejunum. Thus, the extension of jejunal tube is adjusted to the patient's unique anatomical requirements.

With the jejunal tube 32 advanced to the proper extent, for example as illustrated in FIG. 5, the gastric tube may then be displaced along the jejunal tube so as to enter the stoma and penetrate the interior of the stomach cavity. A suitable surgical lubricant is used to assist the insertion of the tube 11 through the stoma 16. When the balloon portion 13 of the gastric tube 11 is positioned within the stomach cavity, the syringe 23 is applied to the valve 24 and fluid is introduced into the fluid lumen 22 to introduce pressure fluid into the balloon 13 and cause it to extend, as shown in FIG. 5. With the balloon extended, the syringe may be withdrawn from the valve and the self-sealing nature of the valve will maintain the balloon extended. The gastric tube 11 is then retracted so as to firmly seat the balloon against the internal wall of the stomach surrounding the stoma 16, care being exercised to avoid longitudinal displacement of the jejunal tube from its adjusted position within the small intestine. With the balloon 13 of the gastric tube firmly seated against the interior wall of the stomach, the ring 14 is displaced along the exterior of the gastric tube to engage flush against the skin surrounding the stoma 16 so as to firmly anchor the gastric tube in place within the stoma 16. The plug 38 is then applied around the jejunal tube 32 to anchor the jejunal tube against inadvertent displacement, as shown in FIG. 4 and FIG. 6. The guide element within the jejunal tube is removed so as to free the bore of the jejunal tube 32 for use as a jejunal lumen for the introduction of a suitable fluent material into the jejunum through the ports 36.

While a particular embodiment of a feeding and medicating device has been herein illustrated and described, it is not intended to limit the invention to the specific embodiment illustrated, but changes and modifications may be made therein and thereto within the scope of the following claims.

I claim:

1. A multi-lumen enteral feeding and medicating device for supplying fluent materials to a patient having a stoma penetrating into the stomach, comprising:

an elongated jejunal feeding tube adapted to pass through the stoma and having an inlet end adapted to be positioned externally of the patient and an elongated distal end adapted to extend beyond the stoma through the patient's stomach and into the jejunum;

a gastric feeding tube coaxial with said jejunal tube and having a gastric lumen defined by the hollow interior of the gastric tube surrounding the jejunal tube with a distal end having an outlet within the patient's stomach and an inlet end positioned externally of the patient;

said gastric tube having a balloon portion near its distal end operable to be extended to lodge against the stomach wall surrounding the stoma and a fluid lumen open at its distal end to the interior of said balloon and extending along the length of said gastric tube;

a support ring mounted on the external part of said gastric tube to engage the body of the patient surrounding the external opening of the stoma;

a feeding attachment at the inlet end of said gastric tube having a gastric inlet passage communicating through said gastric lumen with said gastric lumen outlet, a valve line passage communicating with said fluid lumen for applying positive and negative fluid pressure to said fluid lumen to thereby extend and retract said balloon, and a jejunal passage receiving said jejunal tube, the improvement wherein said jejunal tube is mounted for longitudinal sliding displacement within said jejunal passage and within the distal end of said gastric tube to enable relative longitudinal displacement between said jejunal tube and said gastric tube to permit adjustment of the extension of said jejunal tube beyond the distal end of said gastric tube, said jejunal tube being sealed within said jejunal passage so as to close the gastric lumen around the exterior surface of said jejunal tube to afford to introduction of a first fluent material through said gastric inlet passage and said gastric lumen into the interior of the patient's stomach adjacent the distal end of the gastric tube;

said jejunal tube providing an uninterrupted lumen extending through said gastric tube and said stomach and having at its distal end outlet means for introducing a second fluent material into the jejunum.

2. A multi-lumen enteral feeding and medicating device according to claim 1 wherein the outer dimension of said jejunal feeding tube is less than the hollow interior dimension of said gastric tube whereby said gastric lumen comprises an annular passage extending from said feeding attachment to said distal end, the interior end of said gastric tube at the distal end being of reduced dimension so as to sealingly engage the outside of said jejunal feeding tube, said outlet of said gastric feeding tube comprising ports communicating with said annular passage adjacent said reduced portion of the gastric tube.

3. A multi-lumen enteral feeding and medicating device according to claim 1 wherein said jejunal tube has an outside dimension substantially less than the inside dimension of said jejunal passage to allow free longitudinal displacement of said jejunal tube within said passage, said jejunal tube having an annular plug slidably mounted thereon for longitudinal displacement on the outside of said tube for engagement between said tube and said jejunal passage to provide a seal to seal said tube within said passage.

4. A multi-lumen enteral feeding and medicating device according to claim 1 wherein said gastric inlet passage in said feeding attachment is aligned coaxially with said gastric feeding tube, and said jejunal passage is aligned at an obtuse to the axis of said gastric lumen.

5. A multi-lumen enteral feeding and medicating device according to claim 1 wherein said jejunal passage in said feeding attachment is aligned coaxially with said gastric lumen and said gastric inlet passage is disposed at an angle to the axis of said gastric lumen.

6. A device according to claim 1 including a closure for said gastric inlet passage, said closure having a sealing plug adapted to enter the passage and close the same and having an external flexible tether secured to the outside of said gastric tube inlet passage.

7. A device according to claim 1 wherein said jejunal lumen is closed at its distal terminus and has ports in said jejunal tube adjacent said terminus to define said outlet means of the jejunal lumen.

8. A method for the placement of a multi-lumen enteral feeding and medicating device for supplying fluent materials to a patient having a stoma penetrating into the stomach comprising the steps of providing an enteral feeding and medicating device having a hollow gastric feeding tube with an internal gastric lumen and an elongated jejunal feeding tube slidably mounted within said gastric lumen, positioning said gastric feeding tube within the stoma with the distal end of said feeding tube positioned within the stomach;

advancing the jejunal tube beyond the distal end of said gastric tube causing the distal end of the jejunal tube to pass through the stomach into the jejunum, and adjusting the extension of said jejunal tube to the patient's anatomical requirements; and anchoring said jejunal tube within the gastric tube and sealing the entryway of said jejunal tube into the gastric lumen.

9. A method according to claim 8 including the step of anchoring the gastric tube into the stoma after to advancing said jejunal tube through the stomach.

10. A method according to claim 9 wherein the step of anchoring the gastric tube within the stoma includes providing the gastric tube with a balloon adjacent its distal end, said balloon being adapted for extension and retraction by application of positive and negative fluid pressure thereto, inserting said gastric tube through the stoma while the balloon is retracted and extending said balloon to surround the internal stoma opening in the stomach and to advancing said support ring to engage the body of the patient to impede the migration of gastric juices into the stoma around the outside of said gastric tube.

11. A method according to claim 8 including the step of providing an electromagnetic image of the jejunum, and using a guide element which is opaque to electromagnetic imaging to advance the jejunal tube into the desired position within jejunum by observing said electromagnetic image.

12. A method according to claim 8 including the step of threading a stiff flexible guide element through the lumen of said jejunal tube prior to advancing it through the gastric lumen, using said stiff flexible guide element to guide the distal end of said jejunal tube into the desired position, and withdrawing the stiff flexible guide element from the jejunal lumen so as to free the lumen for passage of fluent material.

* * * * *